US012655231B2

(12) United States Patent
Guo

(10) Patent No.: US 12,655,231 B2
(45) Date of Patent: Jun. 16, 2026

(54) NATIVE CELL MEMBRANE NANOPARTICLE AND METHODS OF USE THEREOF

(71) Applicant: Virginia Commonwealth University, Richmond, VA (US)

(72) Inventor: Youzhong Guo, Glen Allen, VA (US)

(73) Assignee: Virginia Commonwealth University, Richmond, VA (US)

( * ) Notice: Subject to any disclaimer, the term of this patent is extended or adjusted under 35 U.S.C. 154(b) by 641 days.

(21) Appl. No.: 18/001,413

(22) PCT Filed: Jun. 2, 2021

(86) PCT No.: PCT/US2021/035388
§ 371 (c)(1),
(2) Date: Dec. 9, 2022

(87) PCT Pub. No.: WO2021/252236
PCT Pub. Date: Dec. 16, 2021

(65) Prior Publication Data

US 2023/0295349 A1 Sep. 21, 2023

Related U.S. Application Data

(60) Provisional application No. 63/037,345, filed on Jun. 10, 2020, provisional application No. 63/037,334, filed on Jun. 10, 2020, provisional application No. 63/037,322, filed on Jun. 10, 2020, provisional application No. 63/037,362, filed on Jun. 10, 2020.

(51) Int. Cl.
*C07K 17/08* (2006.01)
*C07K 1/14* (2006.01)
*C07K 1/36* (2006.01)

(52) U.S. Cl.
CPC ................ *C07K 17/08* (2013.01); *C07K 1/14* (2013.01); *C07K 1/36* (2013.01)

(58) Field of Classification Search
CPC ............. C07K 17/08; C07K 1/14; C07K 1/36
See application file for complete search history.

(56) References Cited

U.S. PATENT DOCUMENTS 9,458,131 B2 10/2016 Yoon et al.
2014/0303063 A1 10/2014 Kropf et al.

OTHER PUBLICATIONS

Juarez et al. "From polymer chemistry to structural biology: The development of SMA and related amphipathic polymers for membrane protein extraction and solubilization" Chemistry and Physics of Lipids 221 (2019) 167-175. (Year: 2019).*

(Continued)

*Primary Examiner* — Jezia Riley
(74) *Attorney, Agent, or Firm* — WCF IP

(57) ABSTRACT

Provided are a Native Cell Membrane Nanoparticle (NCMN) system and methods of using the NCMN polymers to extract and/or purify one or more membrane proteins. The NCMN system includes at least one NCMN polymer and one or more membrane proteins in their native lipid bilayer membrane. A method of using the NCMN system to extract or isolate the one or more membrane proteins in the form of NCMN system without the use of a detergent while maintaining the protein's native structure and functional activity is provided.

6 Claims, 8 Drawing Sheets

(56) References Cited

OTHER PUBLICATIONS

Qiu et al. "Structure and activity of lipid bilayer within a membrane-protein transporter" by Qiu et al. PNAS, vol. 115, No. 51, pp. 12985-12990, 2018. (Year: 2018).*

Qiu et al. Structure and activity of lipid bilayer within a membrane-protein transporter, PNAS, vol. 115, No. 51, Dec. 18, 2018.

Yang et al. A native cell membrane nanoparticles system allows for high-quality functional proteoliposome reconstitution, BBA Advances, vol. 1 Apr. 2021.

* cited by examiner

NATIVE CELL MEMBRANE NANOPARTICLE AND METHODS OF USE THEREOF

STATEMENT OF GOVERNMENT INTEREST

This invention was made with government support under Grant No. R01 GM132329 awarded by the National Institutes of Health. The government has certain rights in the invention.

FIELD OF THE INVENTION

The disclosure generally relates to a Native Cell Membrane Nanoparticle (NCMN) system and the methods of using such system for extracting, isolating and/or solubilizing a membrane protein. In particular, the invention provides a NCMN system which comprises one or more NCMN polymers and a method of using such polymers for extracting the membrane protein of interest while maintaining functional activity and native structure of the isolated membrane protein.

BACKGROUND

Transmembrane proteins, including channels, transporters, receptors and enzymes, carry out a wide range of vital roles, including controlling what enters and leaves a cell and mediating intracellular communication. Consequently, they are the target of a large number of prescribed drugs, thus there is great interest in understanding the structure and function of this class of proteins. Due to their location within a membrane bilayer and insolubility in water, extracting or solubilizing a membrane protein embedded in a lipid bilayer generally involves buffers and/or reagents containing harsh detergents or surfactants, which destabilize the membrane and interact with the protein, creating a micellar structure around the regions that would normally be in the membrane. However, the use of detergents may present several difficulties, such as regulating efficient extraction concentration of detergent without also denaturing the protein of interest, stripping away annular lipids from the protein which are crucial for function, and/or loss of lateral pressure provided by the membrane which affects both structure and function of the isolated protein. To overcome such limitations, nanodisc is used to stabilize membrane proteins after extracting from cell membrane with a detergent. Another method used in the art involves bicelle, apolipodisc or saposin, which again stabilizes the membrane protein after the detergent-based extraction. However, as apparent from the description, all of the listed strategies of stabilizing the membrane protein still involves the use of detergents in their extraction procedure. For example, U.S. Pat. No. 9,458,191 to Chromy describes a nanolipoprotein particle composition and methods to capture, solubilize and purify membrane proteins. Although the nanolipoprotein composition is able to preserve some structural integrity and activity of the isolated membrane proteins, the disclosed method in Chromy requires a step of mixing the membrane to at least three temperature transition cycles in presence of a detergent to solubilize the target protein. In addition, this method, along with other current methods for membrane protein extraction, notes an additional step of removing the detergent after the isolation of a target protein.

Recently, a styrene-maleic acid (SMA) co-polymer has been used in an alternative method that allows the membrane protein to be extracted without the use of detergents.

The SMA co-polymer inserts into a biological membrane and forms small discs of bilayer encircled by the polymer, which are also called lipodisqs or native nanodiscs. The SMA co-polymer forms nanoparticles by absorbing, destabilizing and disrupting the cell membrane by a pH-dependent mechanism. The resulting SMA lipid particle (SMALP)-encapsulated proteins have been shown to be more thermostable. Despite the effective detergent-free membrane protein isolation capability of SMALP, several shortcomings of SMALP have also been apparent: i) being unstable or insoluble in certain environments (e.g., low pH, presence of divalent ions); ii) limited compatibility to only certain groups of membrane proteins (e.g., not compatible for ABC transporters); and iii) involving multiple steps in the preparation stage.

Thus, there is a need in the art for an improved transmembrane protein extraction system with simple and effective isolating properties and ability to maintain the structure and activity of the membrane protein in a detergent-free manner.

SUMMARY OF THE INVENTION

An object of the invention is a native cell membrane nanoparticle (NCMN) system and a method of using the NCMN system for extracting membrane proteins while preserving native structures and functional activities of the proteins. The NCMN system comprises one or more NCMN polymers selected from the group of polymers 1-4 or combinations thereof. One of the advantageous features of the present invention includes an excellent solubility of the NCMN system in aqueous condition and a stability in various environments, especially in low temperature (e.g., 4° C.) and/or low pH (e.g., pH=4-6) conditions. The present invention provides novel NCMN polymers for membrane protein research and technology, including effective solubilizing agents and methods for solubilizing, isolating, characterizing membrane proteins, including intrinsic membrane proteins.

One aspect of the disclosure provides a NCMN system comprising a NCMN polymer 1 (NCMNP2a) having the structure of formula I:

Formula I

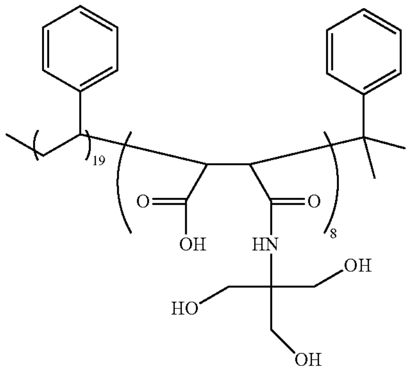

In one embodiment, the NCMN system comprises a NCMN polymer 2 (NCMNP2) having the structure of formula II:

Formula II

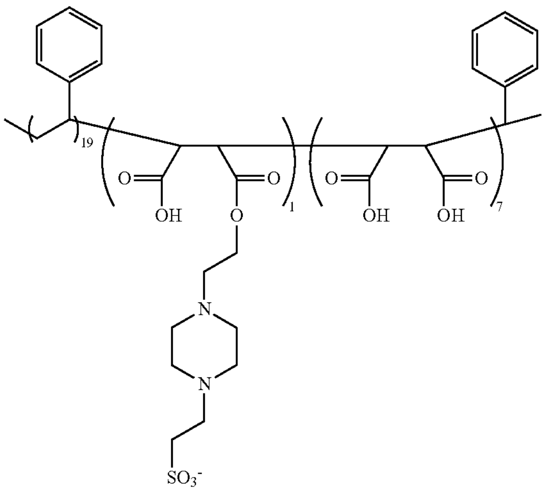

In another embodiment, the NCMN system comprises a NCMN polymer 3 (NCMNP3) having the structure of formula III:

Formula III

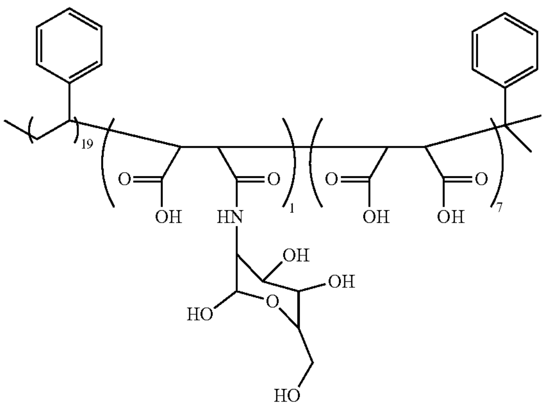

In another embodiment, the NCMN system comprises a NCMN polymer 4 (NCMNP4) having the structure of formula IV:

Formula IV

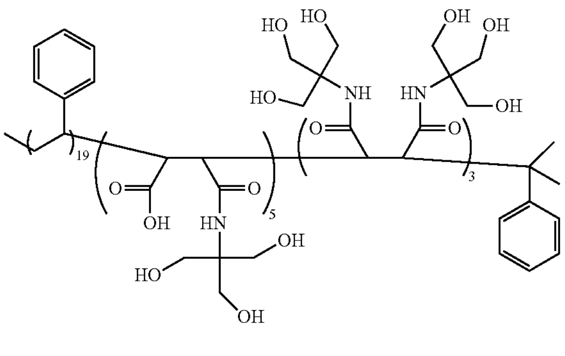

In yet another embodiment, the NCMN system comprises one or more NCMN polymers selected from the group consisting of NCMN polymers 1-4 or combinations thereof, having Formulas I-IV.

Another aspect of the disclosure also provides a NCMN system comprising at least one NCMN polymer selected from the group consisting of NCMN polymers 1-4, one or more membrane proteins and a portion of the protein's native membrane. In these embodiments, the membrane proteins may have intimate, functional, preserved and stabilizing interactions with the co-isolated patch of native membrane around the proteins. Depending on the properties and sizes of the membrane proteins, one or more NCMN polymers are selected from the group of NCMN polymers 1-4.

Another aspect of the disclosure provides a method of extracting, isolating, solubilizing or characterizing one or more membrane associated proteins from a cell membrane or a lipid bilayer by using the NCMN system. The method also provides a membrane-active-polymer assisted membrane protein purification and reconstitution into a proteoliposome without the presence of a detergent. The method of extracting membrane proteins or associated proteins comprises steps of: contacting a cell membrane with a sufficient amount of NCMN polymers; extracting or isolating one or more membrane proteins embedded in their native membrane within the NCMN system; and maintaining the native structures and functional activities of the membrane proteins. The methods herein described can be used, in several embodiments, to assemble, extract, solubilize and/or purify many kind of membrane proteins or membrane associated proteins of interest, including integral membrane proteins and other proteins difficult to isolate without applying detergent. In some embodiments, the NCMN system may comprise at least one NCMN polymer. In other embodiments, the NCMN system may comprise combinations of NCMN polymers selected from the group consisting of NCMN polymers 1-4 having Formulas I-IV.

Additional features and advantages of the present invention will be set forth in the description of disclosure that follows, and in part will be apparent from the description of may be learned by practice of the disclosure. The disclosure will be realized and attained by the compositions and methods particularly pointed out in the written description and claims hereof.

(also known as NCMNP2 or $S^R$MAP2) $^1H$ NMR spectrum (A) and $^{13}C$ NMR spectrum (B) are shown.

Figure 1:
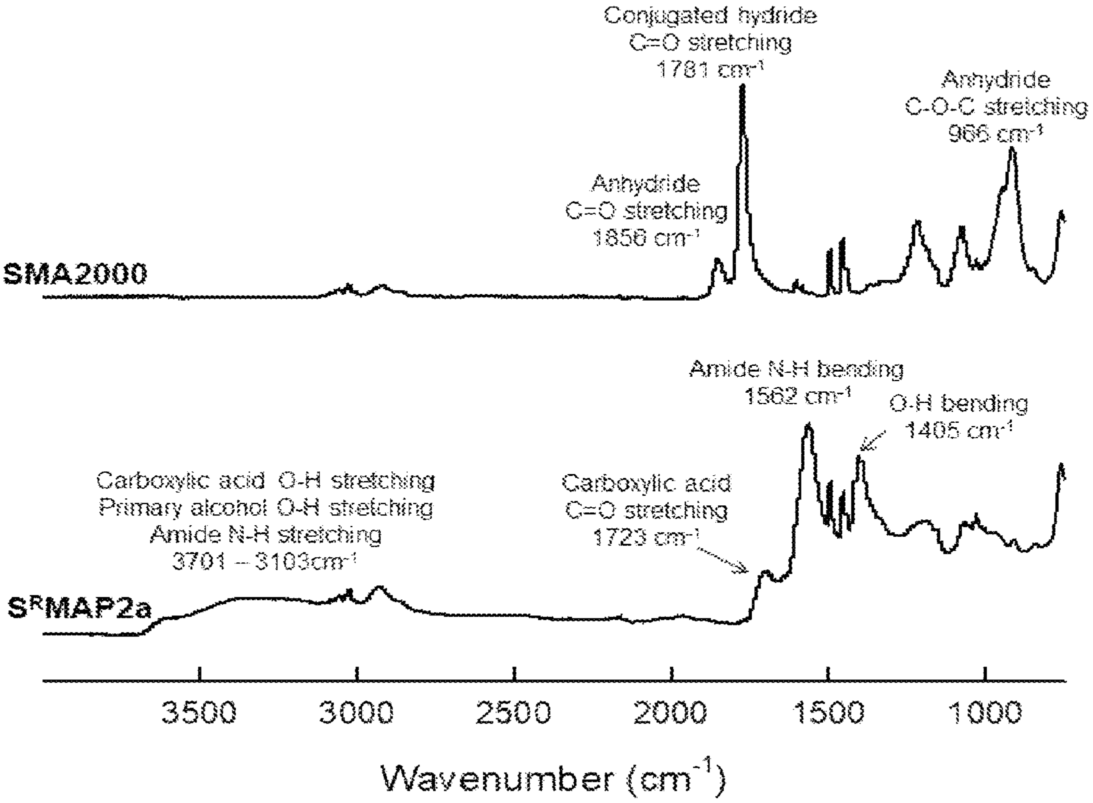
FIG. 1 shows IR spectra of SMA2000 material (starting material) and NCMN system polymer 1 (also known as NCMNP2a or $S^R$MAP2a).
Figure 2A:
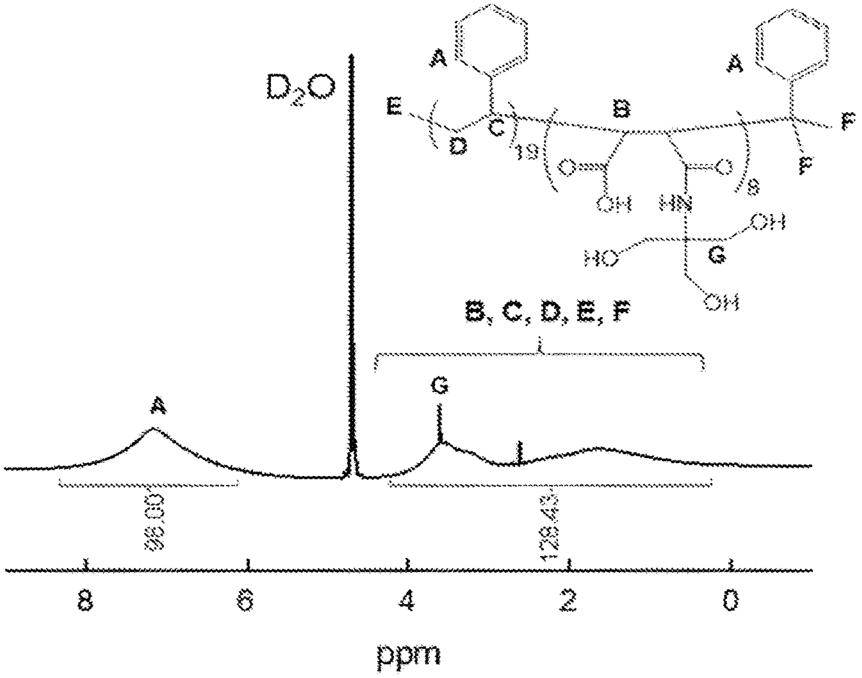
FIG. 2A-B show NMR spectra of NCMN system polymer 1 with corresponding chemical structure of the polymer 1 (also known as NCMNP2a or $S^R$MAP2a)$^1$H NMR spectrum (A) and $^{13}$C NMR spectrum (B) are shown.
Figure 2B:
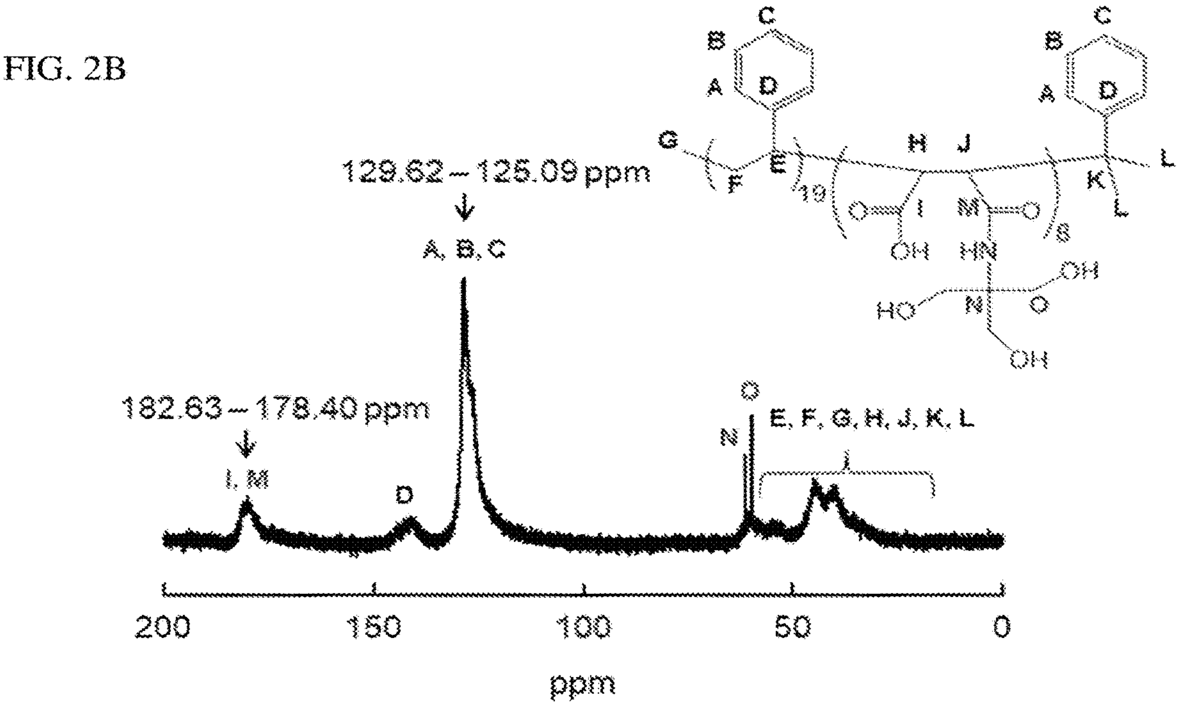
Figure 3:
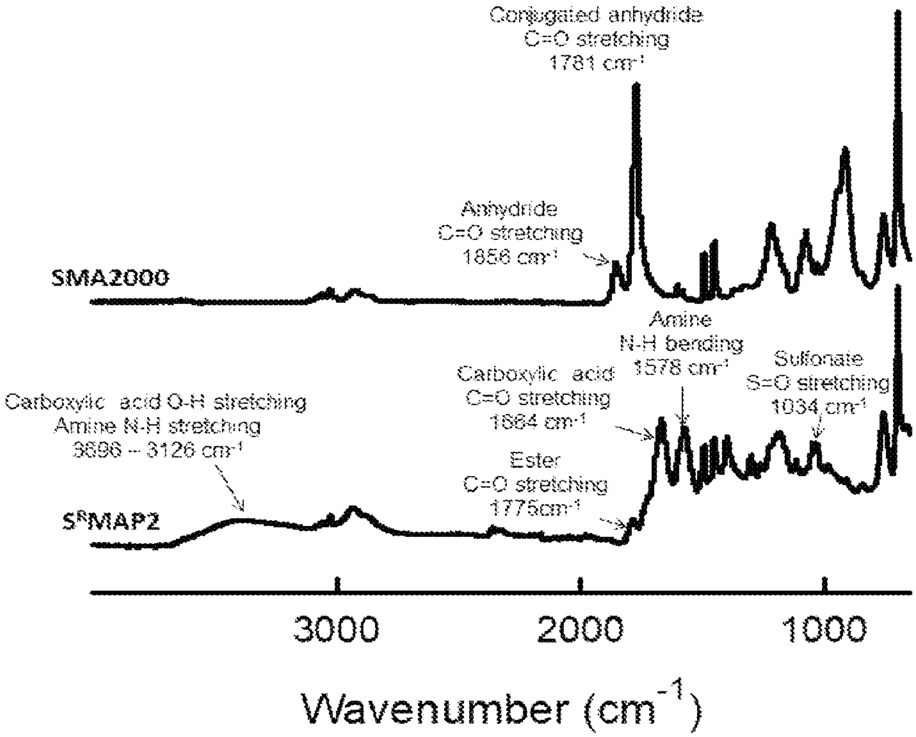
FIG. 3. shows IR spectra of SMA2000 material (starting material) and NCMN system polymer 2 (also known as NCMNP2 or $S^R$MAP2).
Figure 4A:
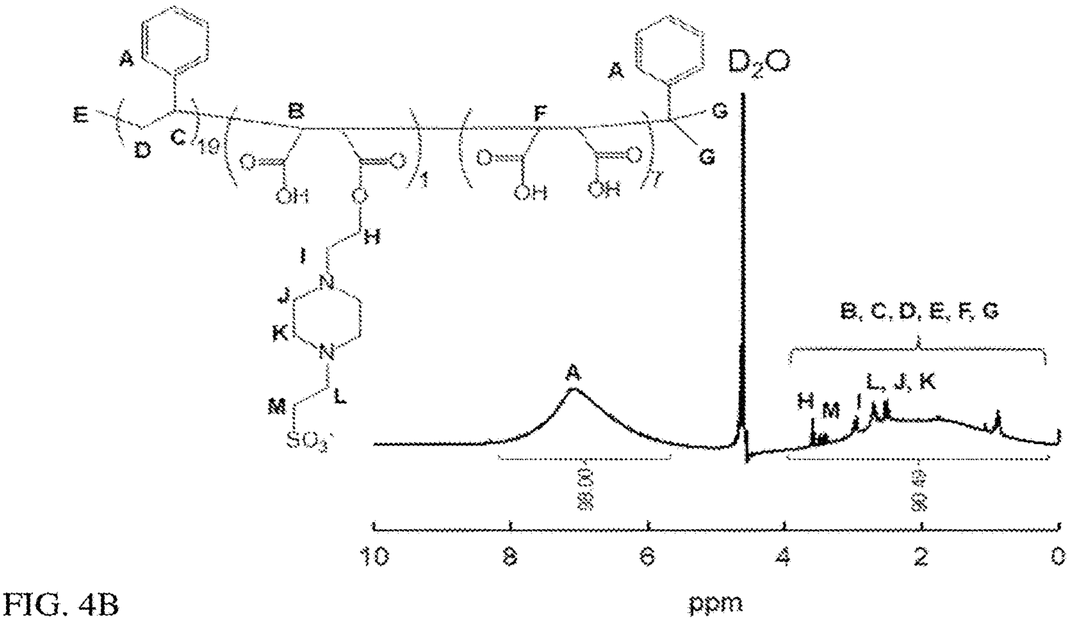
FIG. 4A-B show NMR spectra of NCMN system polymer 2 with corresponding chemical structure of the polymer 2
Figure 4B:
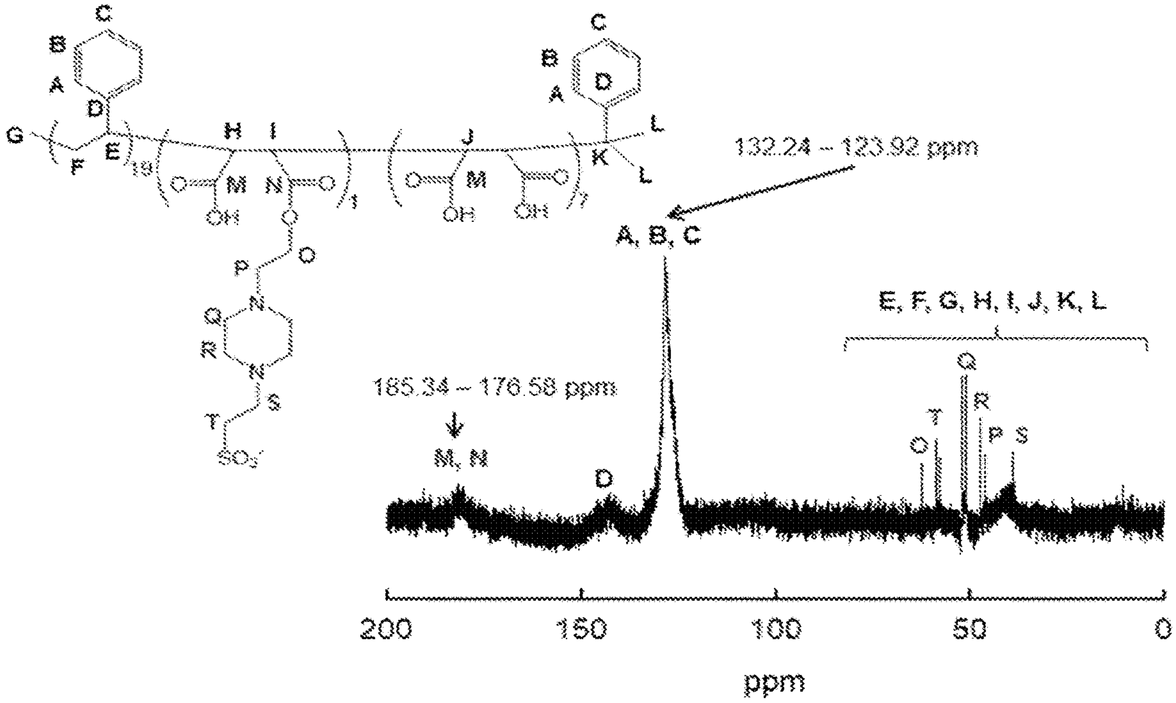
Figure 5:
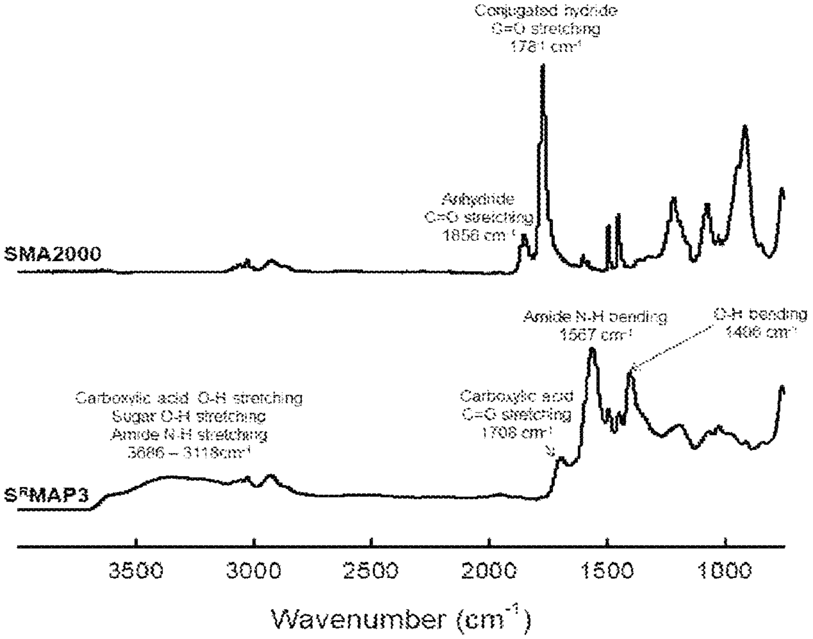

FIG. 5 shows IR spectra of SMA2000 material (starting material) and NCMN system polymer 3 (also known as NCMNP3 or $S^R$MAP3).

Figure 6A:
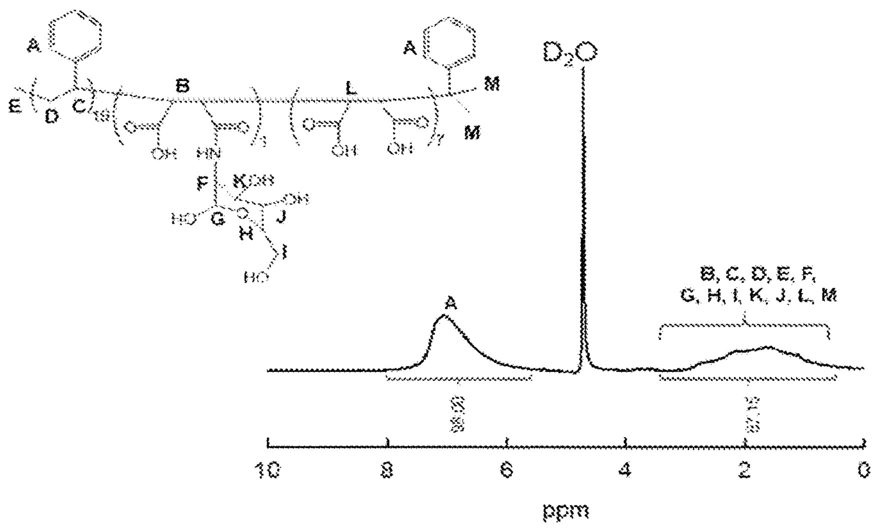
Figure 6B:
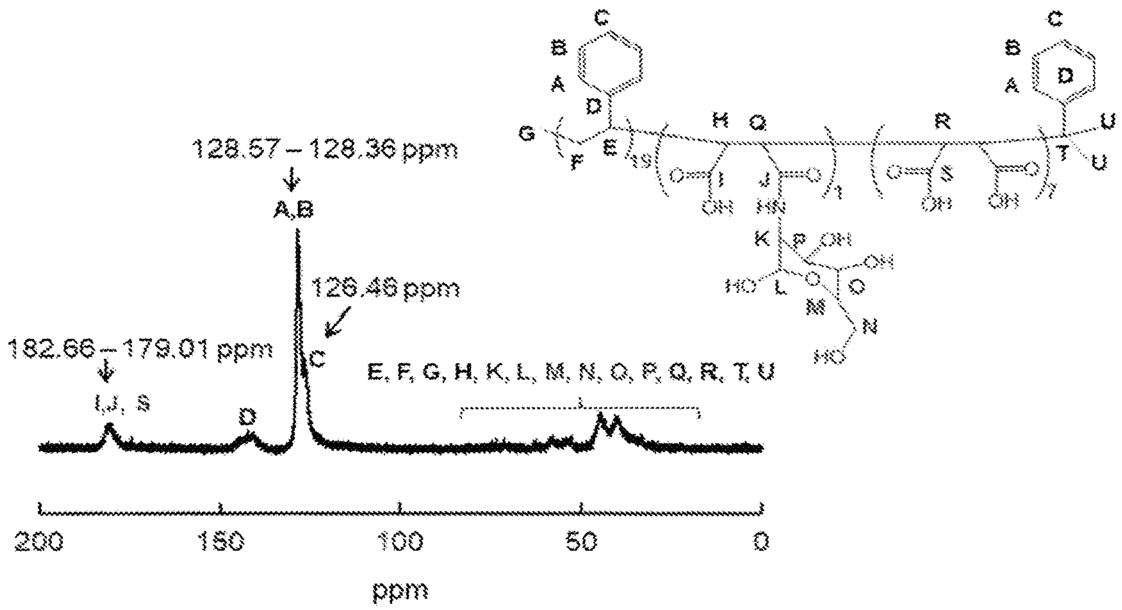

FIG. 6A-B show NMR spectra of NCMN system polymer 1 with corresponding chemical structure of the polymer 3 (also known as NCMNP3 or $S^R$MAP3) $^1H$ NMR spectrum (A) and $^{13}C$ NMR spectrum (B) are shown.

Figure 7:
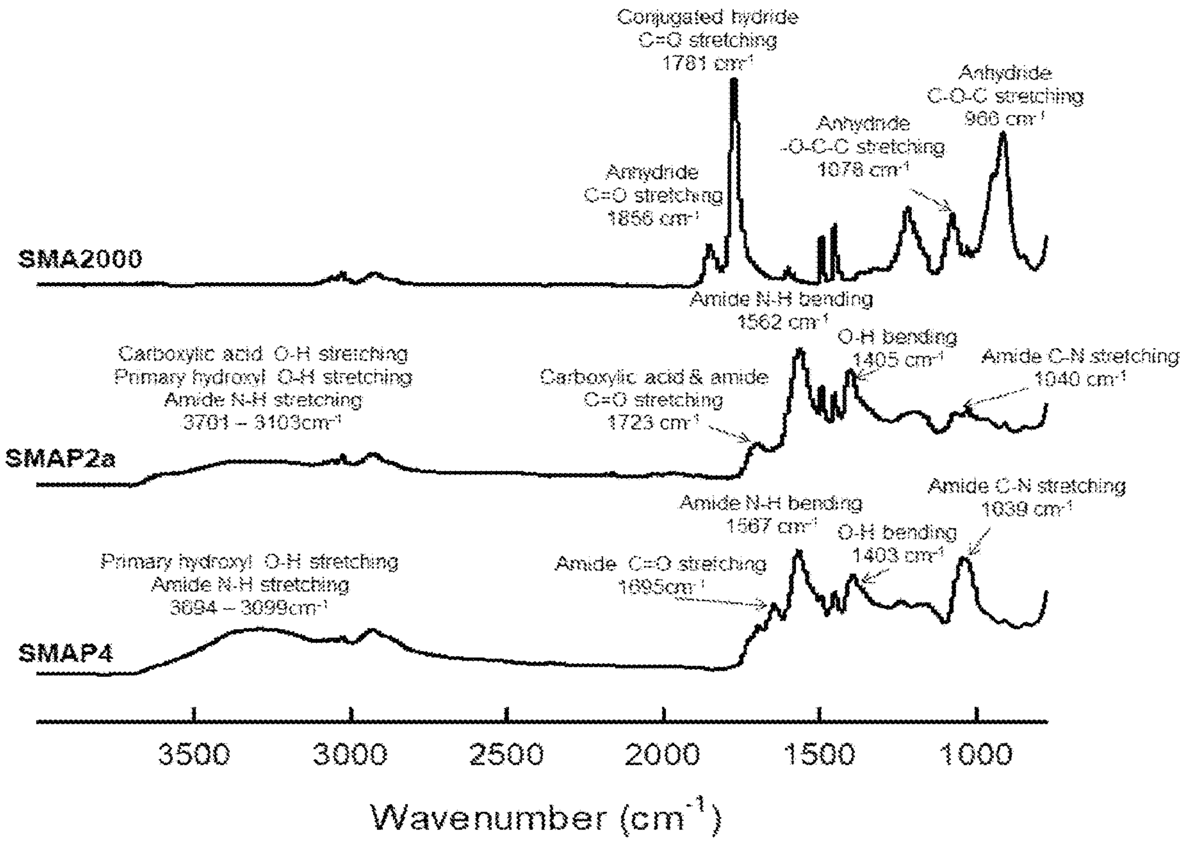

FIG. 7 shows IR spectra of SMA2000 material (starting material), $S^R$MAP2a (NCMN system polymer 1) and NCMN system polymer 4 (also known as NCMNP4 or $S^R$MAP4).

Figure 8A:
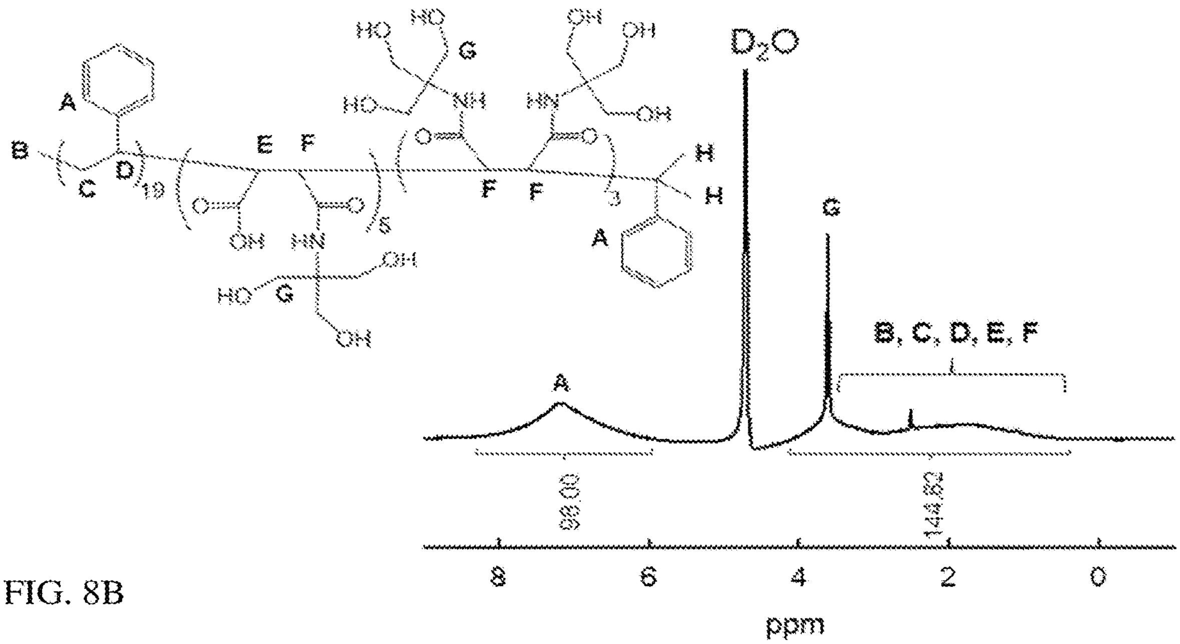
Figure 8B:
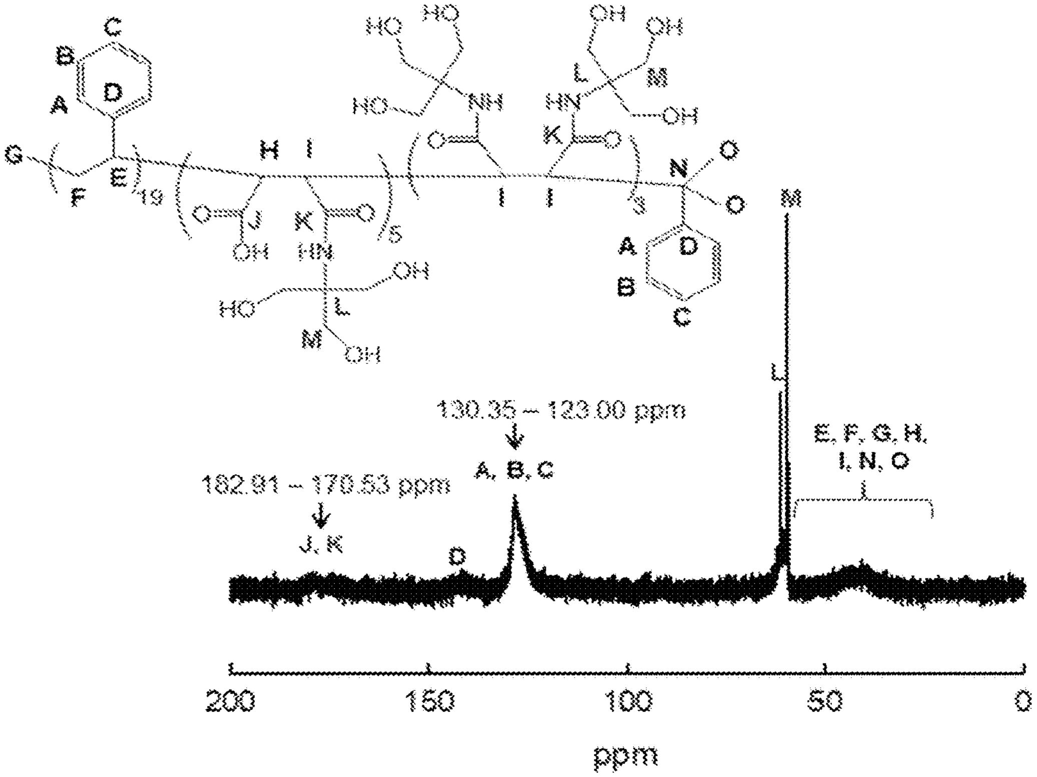

FIG. 8 A-B show NMR spectra of NCMN system polymer 4 with corresponding chemical structure of the polymer 4 (also known as NCMNP4 or $S^R$MAP4) $^1H$ NMR spectrum (A) and $^{13}C$ NMR spectrum (B) are shown.

DETAILED DESCRIPTION

The preferred embodiments of the present disclosure are directed toward a Native Cell Membrane Nanoparticles (NCMN) system and a method of using such system to extract, isolate and/or purify one or more membrane proteins for preserving the native lipid environment and maintaining the native structure and activity of the target membrane proteins. The NCMN system provides an improved tolerance to low pH conditions during the protein extraction. Further, the NCMN polymers can isolate and extract materials in a simplified step by eliminating the use of detergents. As such, detergent titration and optimization for reconstituting the isolated protein, as well as several wash steps for removal of detergent after the reconstitution, are not required, thus increasing the efficiency and overall yield of NCMN containing liposomes.

One aspect of the present invention relates to novel NCMN polymers 1-4.

In one embodiment, the NCMN system comprises a NCMN polymer 1 (NCMNP2a) having the structure of Formula I:

Formula I

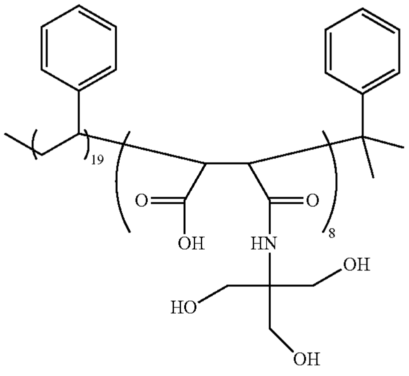

In one embodiment, the NCMN system comprises a NCMN polymer 2 (NCMNP2) having the structure of Formula II:

Formula II

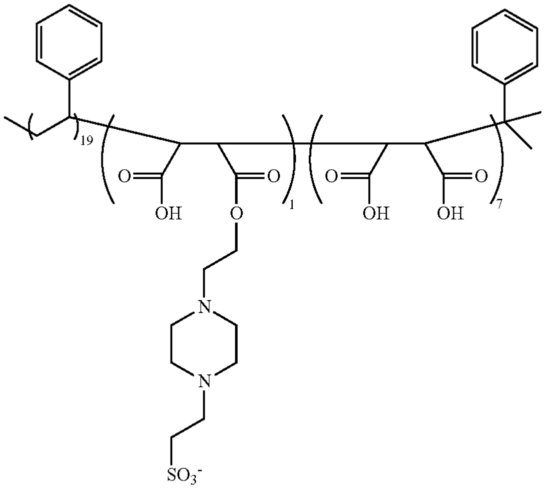

In another embodiment, the NCMN system comprises a NCMN polymer 3 (NCMNP3) having the structure of Formula III:

Formula III

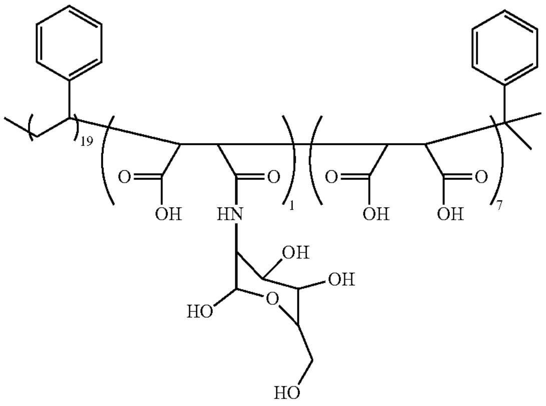

In another embodiment, the NCMN system comprises a NCMN polymer 4 (NCMNP4) having the structure of Formula IV:

Formula IV

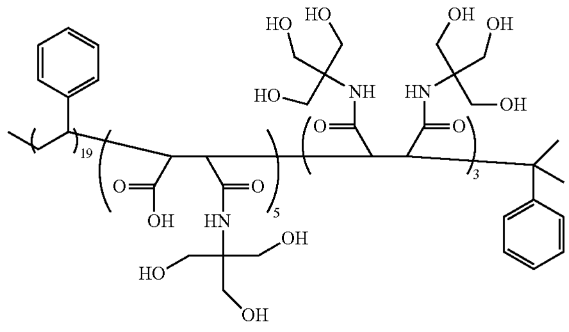

In yet another embodiment, the NCMN system comprises one or more NCMN polymers selected from the group consisting of NCMN polymers 1-4 or combinations thereof, having the structures of Formulas I-IV. In preferred embodiments, only one NCMN polymer is selected from the group consisting of NCMN polymers 1-4 and purified to generate homogenous NCMN particles. In some embodiments, the NCMN system may comprise a mixture of all NCMNP2a, NCMNP2, NCMNP3 and NCMNP4. In some embodiments, one or more NCMN polymers may be selected for one or more particular membrane proteins. The selection process of at least one NCMNP polymer in the NCMN system may be based on the pH, temperature, molecular or chemical structure, functional activity or any other factors of a specific target membrane protein and/or the lipid bilayer environment of the protein. The NCMN system may be used for membrane proteins in a condition at a low pH (i.e., pH<6, 5, 4, 3), a neutral pH (i.e., pH=7) and/or a high pH (i.e., pH>8). In some embodiments, additional pH-buffer modifying solution may be included. One or more selected NCMN polymers in the system may be stable in a certain pH conditions to preserve the native structure of the target membrane protein.

In preferred embodiments, the NCMN system may comprise one or more NCMN polymer-encapsulated membrane proteins in their native structures. The term "Native structure", "Native form", "Native environment" or "Native state", as used herein, refers to a biochemical acceptable formation of a secondary or tertiary or quaternary structures of proteins when the proteins are expressed in their designated cellular locations. The native state of a protein is also defined herein as a state where the proteins are properly folded and assembled with operative structure and function. The proteins in their native states with intact structures that are not altered by heat, chemicals, enzyme reaction or other denaturants are referred to "native proteins".

The term "membrane protein, "membrane associated protein", "target protein" or "target membrane protein" as used herein indicates any protein having a structure that is suitable for attachment to or association with a biological membrane or biomembrane (i.e., an enclosing or separating amphipathic layer that acts as a barrier within or around a cell). In particular, target proteins include proteins that contain large regions or structural domains that are hydrophobic (the regions that are embedded in or bound to the membrane); those proteins can be extremely difficult to work with in aqueous systems, since when removed from their normal lipid bilayer environment those proteins tend to aggregate and become insoluble. Accordingly, target proteins are proteins that typically can assume an active form wherein the target protein exhibits one or more functions or activities, and an inactive form wherein the target protein do not exhibit those functions/activities. Exemplary target proteins include, but are not limited to, membrane proteins, i.e., proteins that can be attached to, or associated with the membrane of a cell or an organelle, such as integral membrane proteins (i.e., proteins or assembly of proteins that are permanently attached to the biological membrane), or peripheral membrane proteins (i.e., proteins that adhere only temporarily to the biological membrane with which they are associated). Peripheral membrane proteins are proteins that attach to integral membrane proteins or penetrate the peripheral regions of the lipid bilayer with an attachment that is reversible. Generally, integral membrane proteins may be separated from the biological membranes using detergents, nonpolar solvents, or sometimes denaturing agents. However, in preferred embodiments, the systems and methods of the present invention are substantially free of detergents or any other harsh denaturing agents. As used herein, the term "substantially free" means less than 0.01 wt. %. In other embodiments, the system may be free of a detergent but contain one or more nonpolar solvents.

Some exemplary membrane proteins include, but are not limited to, a G protein-coupled receptor, a 5-hydroxytryptamine receptor, an acetylcholine receptor, an adenosine receptor, an angiotensin receptor, an apelin receptor, a bile acid receptor, a bombesin receptor, a bradykinin receptor, a cannabinoid receptor, a chemerin receptor, a chemokine receptor, a cholecystokinin receptor, a Class A Orphan receptor, a dopamine receptor, an endothelin receptor, a formyl peptide receptor, a free fatty acid receptor, a galanin receptor, a ghrelin receptor, a glycoprotein hormone receptor, a gonadotrophin-releasing hormone receptor, a G protein-coupled estrogen receptor, a histamine receptor, a hydroxycarboxylic acid receptor, a kisspeptin receptor, a leukotriene receptor, a lysophospholipid receptor, a lysophospholipid S1P receptor, a melanin-concentrating hormone receptor, a melanocortin receptor, a melatonin receptor, a motilin receptor, a neuromedin U receptor, a neuropeptide FF/neuropeptide AF receptor, a neuropeptide S receptor, a neuropeptide W/neuropeptide B receptor, a neuropeptide Y receptor, a neurotensin receptor, an opioid receptor, an opsin receptor, an orexin receptor, an oxoglutarate receptor, a P2Y receptor, a platelet-activating factor receptor, a prokineticin receptor, a prolactin-releasing peptide receptor, a prostanoid receptor, a proteinase-activated receptor, a QRFP receptor, a relaxin family peptide receptor, a somatostatin receptor, a succinate receptor, a tachykinin receptor, a thyrotropin-releasing hormone receptor, a trace amine receptor, a urotensin receptor, a vasopressin receptor, or a combination of two or more thereof.

The term, "membrane", "lipid bilayer", "membrane forming lipid" or "amphipathic lipid", as used herein, indicates a lipid possessing both hydrophilic and hydrophobic properties that in an aqueous environment assemble in a lipid bilayer structure that consists of two opposing layers of amphipathic molecules known as polar lipids. Each polar lipid has a hydrophilic moiety (e.g., a polar group), such as a derivatized phosphate or a saccharide group, and a hydrophobic moiety (e.g., a long hydrocarbon chain). Exemplary polar lipids include phospholipids, sphingolipids, glycolipids, ether lipids, sterols and alkyl phosphocholines. Amphipathic lipids include but are not limited to membrane lipids, i.e., amphipathic lipids that are constituents of a biological membrane, such as phospholipids like dimyristoylphosphatidylcholine (DMPC) or Dioleoyl phosphoethanolamine (DOPE) or dioleoyl phosphatidylcholine (DOPC). The membrane forming lipid can assume different states in an aqueous environment, including a frozen gel state and/or a fluid liquid-crystalline state, wherein each state is associated with one or more temperatures or pHs at which the particular structural phase is detectable. The NCMN system may include at least a portion of the "native membrane" (i.e., the membrane surrounding the one or more membrane proteins of interest), which may be in a combined form with the one or more membrane proteins and at least one polymer.

The term, "polymer" or "polymer derivative", as used herein, refers to an organic material or polymeric composition consisting of repeated one or more polymerizable units joined together, usually in a line, like beads on a string whereas monomers are the basic building blocks of polymers. The term "nanolipoprotein particle", "nanoparticles", "nanodisc" or "membrane nanoparticles", as used herein indicates a supramolecular complex formed by a membrane forming lipid and a scaffold protein, that following assembly in presence of a target protein also include the target protein.

Both scaffold protein and target protein may constitute protein components of the NCMN system. In some embodiments, the membrane forming lipid constitutes a lipid component of the NCMN system. The terms, "polymer encapsulated" and "polymer embedded", as used herein, are used interchangeably and refer to a state where a portion or entirety of the membrane protein of interest is enclosed, stored or hidden inside a polymer or a system comprising a polymer.

In some embodiments, the methods and systems herein disclosed allow NCMN polymers to incorporate diverse membrane proteins, which include, but are not limited to, integral membrane proteins containing transmembrane alpha-helices and/or beta-sheet structures, as well as, peripheral and monotopic membrane proteins, G protein receptors, Type I, II and III cell-surface receptors and the likes. Membrane proteins that have single or multiple membrane spans can also be functionally solubilized into a NCMN system. Other suitable applications of the NCMN system include various biological fields, such as for detecting microorganisms and/or analysis of bacterial or viral and host protein-protein interactions. The methods of use may also include drug delivery by serving as vehicles for therapeutic based countermeasures.

Another aspect of the disclosure provides a method of extracting, isolating, solubilizing and/or characterizing one or more membrane proteins or membrane associated proteins from a cell membrane or a lipid bilayer in a NCMN system. The method of extracting membrane proteins or associated proteins comprises steps of: contacting a cell membrane with a sufficient amount of one or more NCMN polymers; extracting or isolating one or more membrane proteins embedded in their native membrane within the NCMN system. For contacting a cell membrane with at least one NCMN polymer, the cell membrane and the at least one NCMN polymer may be mixed at a ratio of about 5:1 to 1:10, preferably about 4:1 to 1:8, more preferably about 3:1 to 1:5.

The methods herein described can be used, in several embodiments, to assemble, to extract, to solubilize and/or to purify many kind of membrane proteins or membrane associated proteins of interest, including integral membrane proteins and any other proteins difficult to isolate without applying a detergent. In some embodiments, the NCMN system may comprise at least one NCMN polymer. In other embodiments, the NCMN system may comprise combinations of NCMN polymers selected from the group consisting of NCMN polymers 1-4 having Formulas I-IV.

The terms, "extract" and "isolate", as used herein, are used interchangeably and refer to a series of processes intended to isolate one or more proteins from a complex, such as cells, tissues, whole organisms, or cellular membranes. The process described herein refers to a method that separates one or more target membrane proteins and non-protein parts of the mixture (i.e., a portion of the membrane or a lipid bilayer). In addition, the terms may represent extraction and isolation of a specific protein of interest from all other proteins or non-protein components.

The term, "solubilize" as used herein, indicates to make the target membrane protein susceptible or more susceptible to dissolve in a medium and in particular in an aqueous medium. Accordingly, when used with reference to a membrane associated protein the term solubilize indicates making the membrane associated protein soluble or more soluble (susceptible of being dissolved) into an aqueous environment and encompasses solubilizing proteins from a pellet, a solution, a membrane fraction and any other medium and/or preparations wherein the membrane associated protein is comprised alone or in combination with other compounds and/or molecules.

The term, "purify" as used herein, indicate the process of freeing the membrane protein from other components. In particular with reference to a membrane associated protein, the term "purify" indicates the act of separating the membrane associated protein from a medium wherein the protein is comprised together with other molecules and encompasses purification of membrane associated proteins from molecular and/or biological structures such as membranes or molecular complexes. Accordingly, "purifying" a membrane associated protein into a nanoparticle indicates the act of separating the membrane associated protein from an original environment and/or cellular location into the nanoparticle particle.

The term "contacting" refers to the act of touching, making contact, or of bringing to immediate or close proximity, including at the molecular level, for example, to bring about a chemical reaction or physical change, e.g., in a solution or other reaction mixture. An "effective amount" generally means an amount which provides the desired effect. In the present disclosure, an effective amount refers to a concentration or weight of the polymer to entirely or partially extract and/or purify the membrane protein of interest from the cell membrane while maintaining the protein's functional activity and native structure. For example, to extract and/or purify the membrane protein of interest, 1-100 mg, preferably 1-80 mg, or more preferably 1-50 mg of NCMN system may be used. In some embodiments, more than 100 mg of NCMN may be used. In other embodiments, less than 1 mg of NCMN may be used. In addition, an "appropriate time" refers to a time period to obtain the desired effect. For example, in the present disclosure, an appropriate time refers to a time for the NCMN polymers to extract, isolate or purify the membrane protein of interest into a NCMN system. Alternatively, an appropriate time or amount may represent the time or amount that is required for maintaining the isolated membrane protein's structure and functional activity. For example, the isolated membrane protein may be stable in a NCMN system for hours (e.g., any time between 1-24 hours), days (e.g., any day between 1-30 days), months (e.g., any month between 1-12 months) or years (e.g., 1-3 years). The phrase "one or more" is readily understood by one of skill in the art, particularly when read in context of its usage. For example, one or more of NCMN polymers refers to one to three, or one to up to four.

The term, "proteoliposome", as used herein, refers to a system that mimics lipid membranes or liposomes to which a protein has been incorporated or inserted. The proteoliposome (PL) may represent a liposome, a vesicle or any platform that is reconstituted to preserve the embedded protein's (i.e., membrane protein) structural and functional integrities. The polymers described herein can extract membrane proteins from cell membrane for functional study and high-resolution structure determination. The methods and systems may be used in the drug discovery field using membrane proteins as drug targets. In addition, the methods and systems described herein are Cryo-EM compatible. The methods and systems further allow to extract and purify membrane proteins in their functional forms, thus allowing reproduction and/or further analysis of membrane proteins' activity, including catalytic activity, channel transport activity, protein interaction activity, etc. As part of the NCMN system, a NCMN polymer library has been generated and other various derivatives of NCMN polymers may also be included in the system.

EXAMPLE 1

Manufacturing NCMN System

NCMN polymers were made using SMA2000 co-polymer powder purchased from Total Cray Valley instead of flakes as starting materials. NCMN polymers 1-4 were synthesized by a general synthesis method known in the art. Briefly, for the synthesis of NCMNP2a or formula 1, SMA2000:Tris at a molar ratio of 1:3 is used. Tris is first thoroughly dissolved in pure water in a glass reaction bottle, then SMA2000 powder is carefully added into the Tris solution. The reaction bottle is soaked in a mineral oil bath and kept at 110° C. and refluxed for at least 2 hours. During the reaction, frequently check the pH value of the reaction solution. When the pH is lower than pH 5, gradually add some 1M NaOH to bring the pH around 7, but not over 8. When the SMA2000 is completely dissolved, adjust the pH of the reaction solution to pH 7 at room temperature. The newly synthesized polymer can be precipitated with HCl and washed with pure water at lower pH of around 2. After a few cycles of pure water wash, the polymer can be resolved in a proper amount of pure water according to the required concentration (typically 5% W/V) by adjusting the pH to about 7.5 using 1M NaOH. The polymer can be directly used for membrane solubilization or lyophilized for long-term storage at this stage. For the synthesis of NCMNP2 or formula 2 and NCMNP3 or formula 3, HEPES and glycosamine are used instead of Tris. All the other steps are similar. For the synthesis of NCMNP4 or formula 4, the SMA2000:Tris at a molar ratio of 1:6 is used. After the complete desolvation of SMA2000, the reaction system remains at 110° C. for another 6 hours to facilitate the peptide bond formation. Alternatively, a coupling reagent such as Isobutyl chloroformate can also be used to facilitate the reaction. The grafting ratio of tris moiety to the SMA2000 polymer backbone and the corresponding reaction condition needs to be experimentally optimized.

The polymer products were validated and analyzed by IR and NMR as shown in FIG. 1-8. Exemplary preparation method of native cell membrane nanoparticles is described herein. 1.5 to 2 g of pure cell membrane were suspended in NCMN buffer A and homogenized with a Dounce homogenizer in a volume of 25 mL, then 25 mL of 5% stock solution of NCMN polymer was added to bring the total volume to 50 mL in a 50 mL conical tube. The ratio of the wet cell membrane and NCMN polymer was approximately 1 g cell membrane per 0.615 g NCMN polymer; in some cases, this amount of NCMN polymers could be reduced by half without noticeable decreases in yield. The sample was incubated at room temperature for 2 h. The solution was centrifuged at 15,000 g for 30 min, the supernatant was then further centrifuged at 150,000 g for 1 h. The supernatant was then loaded onto a 5 mL NiNTA (GE Health) at a flow rate of 0.5 ml/min using a syringe pump at room temperature. Then, the NiNTA column was washed with 30 mL NCMN buffer B using an AKTA FPLC (GE Healthcare) and 30 mL NCMN buffer C. Finally, protein sample was eluted with NCMN buffer D. The peak fractions were concentrated for final buffer exchange with NCMN buffer E. The final protein samples concentrated to the desired concentration can be used directly for single-particle analysis using electron microscopy including negative stain and cryo-EM or for proteoliposome reconstitution and many other biochemical and biophysical analysis, in including but not limited to NMR, Mass Spectrometry, EPR, X-ray diffraction, Neutron diffraction, and enzyme assay. NCMN buffer A: 50 mM HEPES, pH 8.4, 500 mM NaCl, 5% Glycerol, 20 mM Imidazole, 0.1 mM TCEP. NCMN buffer B: 25 mM HEPES, pH 7.8, 500 mM NaCl, 5% Glycerol, 40 mM Imidazole, 0.1 mM TCEP. NCMN buffer C: 25 mM HEPES, pH 7.8, 500 mM NaCl, 5% Glycerol, 75 mM Imidazole, 0.1 mM TCEP. NCMN buffer D: 25 mM HEPES, pH 7.8, 500 mM NaCl, 5% Glycerol, 300 mM Imidazole, 0.1 mM TCEP. NCMN buffer E: 40 mM HEPES, pH 7.8, 200 mM NaCl, 0.1 mM TCEP.

Detergent free protein reconstitution assisted by NCMN polymers: Lipids dissolved in chloroform were dried under argon while rotating in a glass tube to form a thin lipid film on glass wall, which was further dried under argon for 30 min. Liposomes were formed by either rehydration into appropriate buffers or in the presence of sucrose solution generally used in the art. Proteins in the format of NCMN particles were then added for reconstitution. The generated functional reconstituted proteoliposome in NCMN system are compatible for a plurality of downstream research protocols, such as path-clamp analysis, liposomal efflux assays and Cryo EM. The disclosed polymers may also be applicable to membrane-associated transporters, receptors and enzymes, in addition to the exemplary membrane spanning protein channels shown here.

EXAMPLE 2

Styrene Maleic Acid Copolymer Preparation

We followed a protocol reacting 25 g of SMA®2000 from TOTAL Cray Valley (TCV) and 250 mL 1 M NaOH in a 500 mL round bottom flask. The suspension was stirred and heated to reflux for two hours until everything was dissolved. The reaction was cooled to room temperature. Concentrated HCl was added to the solution until the pH of the solution was lower than 5. The precipitated polymer was then transferred to another container, and 200 mL of 0.6 M NaOH was added. The suspension was stirred at room temperature for 15 hours. The aqueous solution was filtered and lyophilized to collect the final product.

Many factors could affect the result of sample preparation using membrane active polymer for high-resolution structure determination of membrane proteins. The homogeneity of the polymer used for sample preparation could be crucial. We found diisobutylene maleic acid co-polymer (Sokalan CP-9) from BASF has much less homogeneity than SMA copolymer from Cray Valley USA, LLC. The homogeneity of the native cell membrane nanoparticles is a crucial factor for this preparation. This largely depends on the purification strategies. We found that a single-step purification of the native cell membrane protein nanoparticles from affinity column works very well. The free SMA polymer in the sample is also an important factor. We found free SMA polymer in the sample gave heavy background. In order to reduce the background, one should minimize the free SMA polymers in the sample for making cryo-EM grids. Varied procedures were tested in a trial-and-error approach, testing for the quality of particles on EM grids. In tests with many proteins, we have encountered problems with SMA preparations on SEC columns. We surmise that the SMA polymer may interact with column materials. In any case, we consistently find that particles from single-step affinity purification are better on EM grids. In this sense our purification procedure differs from that in other reports. Final 'purification' is then obtained by cryo-EM classification.

EXAMPLE 3

An exemplary protocol of preparing Native Cell Membrane Nanoparticles (NCMN) containing membrane protein for research analysis is described below.

1. Resuspend 1 g of membrane pellet in 10 mL NCMNs Buffer A of Table 1.

TABLE 1

List of NCMN purification buffers.

| Buffer A | Buffer B | Buffer C | Buffer D | Buffer E |
|---|---|---|---|---|
| 50 mM HEPES, pH 8.4 | 25 mM HEPES, pH 7.8 | 25 mM HEPES, pH 7.8 | 25 mM HEPES, pH 7.8 | 40 mM HEPES, pH 7.8 |
| 500 mM NaCl | 500 mM NaCl | 500 mM NaCl | 500 mM NaCl | 200 mM NaCl |
| 5% glycerol | 5% glycerol | 5% glycerol | 5% glycerol | 0.1 mM TCEP |
| 20 mM Imidazole | 40 mM Imidazole | 75 mM Imidazole | 300 mM Imidazole | |
| 0.1 mM TCEP | 0.1 mM TCEP | 0.1 mM TCEP | 0.1 mM TCEP | |

2. Homogenize the resuspended cell membrane sample with a glass Dounce homogenizer at 20° C.
3. Transfer the suspended membrane sample to a 50 mL polypropylene tube and add membrane active polymers stock solution and additional NCMNs Buffer A to bring the sample to a final concentration of 2.5% (w/v) NCMN membrane active polymer. NOTE: Stock solutions of membrane active polymers should be made in double distilled water and can be kept at varying concentrations, but typically 10% (w/v).
4. Shake the sample for 2 h at 20° C.
5. Load the sample into an ultracentrifuge and spin at 150,000×g for 1 h at 20° C.
6. While the sample is being ultra-centrifuged begin to equilibrate a 5 mL Ni-NTA column with 25 mL of NCMNs Buffer A.
7. Collect the supernatant after ultracentrifugation is complete and load it onto 5 mL of Ni-NTA column at room temperature with a flow rate of 0.5 mL/min using a syringe pump.
8. Wash fast protein liquid chromatography (FPLC) lines with enough NCMNs Buffer B (Table 1) to completely flush the system and then connect the column to the FPLC machine.
9. Wash the column with 30 mL of NCMNs Buffer B with a flow rate of 1 mL/min and collect the flow through.
10. Wash the column with 30 mL of NCMNs Buffer C (Table 1) with a flow rate of 1 mL/min and collect the flow through.
11. Elute the protein with 20 mL of NCMNs Buffer D (Table 1) at a flow rate of 0.5 mL/min and collect the sample using a fraction collector and the fractions each being set to 1.0 mL.
12. Store the protein samples at 4° C.
13. Run an SDS-PAGE gel electrophoresis assay in order to check the samples that correspond to peaks observed on the FPLC elution graph.

It is to be understood that this invention is not limited to any particular embodiment described herein and may vary. It is also to be understood that the terminology used herein is for the purpose of describing particular embodiments only, and is not intended to be limiting, since the scope of the present invention will be limited only by the appended claims.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

What is claimed is:

1. A Native Cell Membrane Nanoparticle (NCMN) system comprising:

at least one NCMN polymer selected from the group of NCMN polymers 1-4 or combinations thereof, wherein the polymer 1 has the structure of Formula I;

Formula I

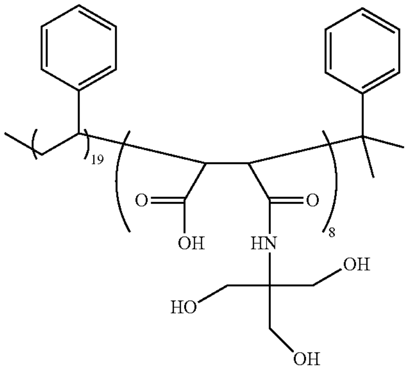

wherein the polymer 2 has the structure of Formula II;

Formula II

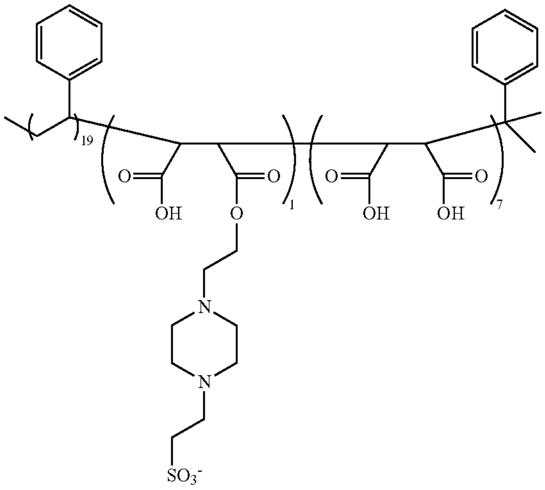

wherein the polymer 3 has the structure of formula III; and

Formula III

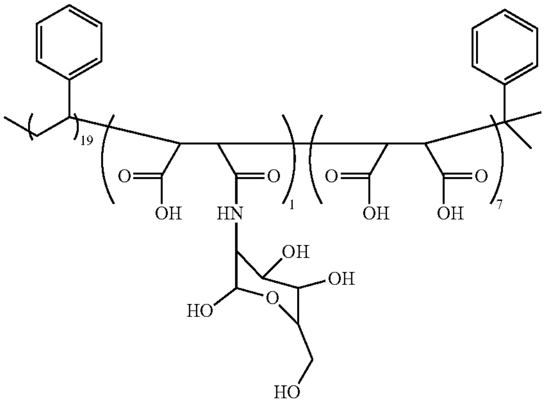

wherein the polymer 4 has the structure of formula IV

Formula IV

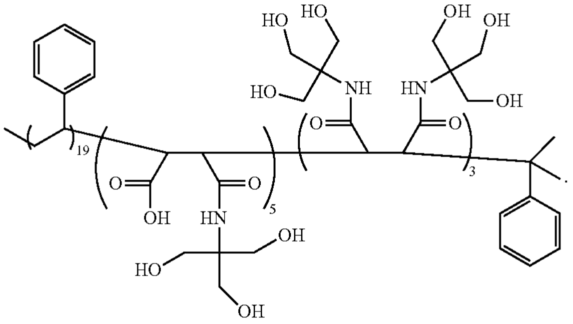

2. The system of claim 1, further comprising one or more membrane proteins.

3. The system of claim 2, wherein the one or more membrane proteins are encapsulated in the at least one NCMN polymer.

4. The system of claim 3, further comprising at least a portion of native membrane of the one or more membrane proteins.

5. The system of claim 1, further comprising one or more membrane proteins that are embedded in a portion of at least one native membrane, wherein a combination of the one or more membrane proteins and the portion of at least one native membrane is encapsulated within the at least one NCMN polymer.

6. The system of claim 1, wherein the system is substantially free of a detergent.

* * * * *